(12) United States Patent
Hnojewyj et al.

(10) Patent No.: US 6,475,182 B1
(45) Date of Patent: Nov. 5, 2002

(54) FLUIDIC MEDIA INTRODUCTION APPARATUS

(76) Inventors: Olexander Hnojewyj, 13925 Trinity Ave., Saratoga, CA (US) 95070; Gregory M Cruise, 3444 Ellery Common, Fremont, CA (US) 94538; Stuart D Edwards, 658 Westridge Dr., Portola Valley, CA (US) 94028; Edward Gough, 134 Crestview Dr., San Carlos Hills, CA (US) 94070

( * ) Notice: Subject to any disclaimer, the term of this patent is extended or adjusted under 35 U.S.C. 154(b) by 0 days.

(21) Appl. No.: 09/140,017

(22) Filed: Aug. 26, 1998

Related U.S. Application Data (63) Continuation-in-part of application No. 09/037,659, filed on Mar. 10, 1998, and a continuation-in-part of application No. 09/021,708, filed on Feb. 10, 1998, now Pat. No. 6,302,898, and a continuation-in-part of application No. 08/963,408, filed on Nov. 3, 1997, now Pat. No. 6,033,401.

(60) Provisional application No. 60/036,299, filed on Mar. 12, 1997.

(51) Int. Cl.[7] .............................................. A61M 37/00
(52) U.S. Cl. ...................... 604/82; 604/96.01; 604/191; 606/214
(58) Field of Search .................. 604/82–92, 93.01, 604/96.01, 98.01, 104–109, 174, 187, 191, 257, 264, 19, 48, 506, 507–510, 164.13, 181–182, 185, 218, 239–243, 523, 528, 533, 912; 222/145.5, 145.6; 606/213–15; 530/381–382

(56) References Cited

U.S. PATENT DOCUMENTS

| | | | |
|---|---|---|---|
| 3,948,259 A | * 4/1976 | Bolduc et al. ............. 128/235 |
| 4,424,833 A | 1/1984 | Spector et al. | |
| 4,555,242 A | 11/1985 | Saudager | |
| 4,631,055 A | * 12/1986 | Redl et al. ..................... 604/82 |
| 4,738,658 A | 4/1988 | Magro et al. | |
| 4,744,364 A | 5/1988 | Kensey | |
| 4,838,280 A | 6/1989 | Haaga | |
| 4,852,568 A | 8/1989 | Kensey | |
| 4,874,368 A | 10/1989 | Miller et al. | |
| 4,890,612 A | 1/1990 | Kensey | |
| 4,891,359 A | 1/1990 | Saferstein et al. | |
| 5,002,051 A | 3/1991 | Dew et al. | |
| 5,021,059 A | 6/1991 | Kewnsey et al. | |
| 5,041,129 A | 8/1991 | Hayhurst et al. | |
| 5,042,985 A | 8/1991 | Elliott et al. | |
| 5,053,046 A | 10/1991 | Janese | |
| 5,061,274 A | 10/1991 | Kensey | |
| 5,089,606 A | * 2/1992 | Cole et al. ..................... 536/54 |
| 5,108,421 A | 4/1992 | Fowler | |
| 5,129,882 A | 7/1992 | Weldon et al. | |
| 5,156,613 A | 10/1992 | Sawyer | |
| 5,159,937 A | 11/1992 | Tremulis | |
| 5,163,906 A | 11/1992 | Ahmadi | |
| 5,171,222 A | 12/1992 | Euteneuer et al. | |
| 5,192,300 A | 3/1993 | Fowler | |

(List continued on next page.)

Primary Examiner—Brian L. Casler
Assistant Examiner—Catherine Serke
(74) Attorney, Agent, or Firm—Myan Kromholz & Manion SC (57) ABSTRACT

A fluidic media introduction apparatus for closing an opening in a vessel wall includes an elongated member with a fluidic media introduction port and a guide wire lumen. The guide wire lumen extends from a proximal portion to a distal portion of the elongated member. A fluidic media mixing chamber is positioned in the elongated member and coupled to a fluidic media introduction port. A fluidic media delivery lumen is coupled to the mixing chamber. A fluidic media advancement port is positioned at the distal portion of the elongated member. An inflatable member is coupled to the distal portion of the elongated member.

14 Claims, 8 Drawing Sheets

U.S. PATENT DOCUMENTS

| | | |
|---|---|---|
| 5,197,971 A | 3/1993 | Bonutti |
| 5,221,259 A | 6/1993 | Weldon et al. |
| 5,222,974 A | 6/1993 | Kensey et al. |
| 5,250,025 A | 10/1993 | Sosnowski et al. |
| 5,275,616 A | 1/1994 | Fowler |
| 5,281,197 A | 1/1994 | Arias et al. |
| 5,282,827 A | 2/1994 | Kensey et al. |
| 5,290,310 A | 3/1994 | Makower et al. |
| 5,292,309 A | 3/1994 | Van Tassel et al. |
| 5,292,332 A | 3/1994 | Lee |
| 5,306,254 A | 4/1994 | Nash et al. |
| 5,324,306 A | 6/1994 | Makower et al. |
| 5,376,069 A * | 12/1994 | Hattler ................ 604/26 |
| 5,383,896 A | 1/1995 | Gershony et al. |
| 5,383,899 A | 1/1995 | Hammerslag |
| 5,411,520 A | 5/1995 | Nash et al. |
| 5,413,571 A | 5/1995 | Katsaros et al. |
| 5,415,657 A | 5/1995 | Taymor-Luria |
| 5,419,765 A | 5/1995 | Weldon et al. |
| 5,437,292 A * | 8/1995 | Kipshidze et al. |
| 5,441,517 A | 8/1995 | Kensey et al. |
| 5,443,481 A | 8/1995 | Lee |
| 5,447,502 A | 9/1995 | Haga |
| 5,486,195 A | 1/1996 | Anderson |
| 5,496,332 A | 3/1996 | Sierra et al. |
| 5,529,577 A | 6/1996 | Hammerslag |
| 5,575,815 A | 11/1996 | Slepian et al. |
| 5,582,596 A | 12/1996 | Fukunaga et al. |
| 5,591,204 A | 1/1997 | Janzen et al. |
| 5,591,205 A | 1/1997 | Fowler |
| 5,601,602 A | 2/1997 | Fowler et al. |
| 5,601,603 A * | 2/1997 | Illi .......................... 606/213 |
| 5,612,050 A | 3/1997 | Rowe et al. |
| 5,626,601 A | 5/1997 | Gershony et al. |
| 5,630,833 A | 5/1997 | Katsaros et al. |
| 5,649,959 A | 7/1997 | Hannam et al. |
| 5,653,730 A | 8/1997 | Hammerslag |
| 5,665,106 A | 9/1997 | Hammerslag |
| 5,665,107 A | 9/1997 | Hammerslag |
| 5,669,934 A | 9/1997 | Sawyer |
| 5,676,689 A | 10/1997 | Kensey et al. |
| 5,700,273 A | 12/1997 | Buelna et al. |
| 5,725,498 A | 3/1998 | Janzen et al. |
| 5,725,551 A | 3/1998 | Myers et al. |
| 5,728,132 A | 3/1998 | VanTassel et al. |
| 5,743,436 A * | 4/1998 | Wilcox et al. ............. 222/137 |
| 5,759,169 A | 6/1998 | Marx |
| 5,759,194 A | 6/1998 | Hammerslag |
| 5,782,860 A | 7/1998 | Epstein et al. |
| 5,814,022 A * | 9/1998 | Antanavich et al. ........ 604/191 |
| 5,830,130 A | 11/1998 | Janzen et al. |
| 5,843,124 A | 12/1998 | Hammerslag |
| 5,855,559 A | 1/1999 | Van Tassel et al. |
| 5,922,009 A | 7/1999 | Epstein et al. |
| 5,935,437 A | 8/1999 | Whitmore |
| 5,951,583 A | 9/1999 | Jensen et al. |
| 5,951,589 A | 9/1999 | Epstein et al. |
| 5,997,516 A * | 12/1999 | Caro et al. .................. 604/264 |
| 6,017,359 A * | 1/2000 | Gershony et al. |
| 6,022,361 A | 2/2000 | Epstein et al. |
| 6,033,427 A * | 3/2000 | Lee .......................... 606/213 |

* cited by examiner

FLUIDIC MEDIA INTRODUCTION APPARATUS

RELATED APPLICATIONS

This application is a continuation-in-part of U.S. Patent Application Ser. No. 09/021,708, filed Feb. 10, 1998, now U.S. Pat. No. 6,302,898, and entitled "Devices for Sealing Punctures in Body Vessels." This application is also a continuation-in-part of U.S. patent application Ser. No. 09/037,659, filed Mar. 10, 1998, and entitled "Universal Introducer," which is itself related to United Provisional Patent Application Ser. No. 60/036,299, filed Mar. 12, 1997. This application is also a continuation-in-part of U.S. patent application Ser. No. 08/963,408, filed Nov. 3, 1997, and entitled "Vascular Sealing Device with Microwave Antenna," now U.S. Pat. No. 6,033,401.

BACKGROUND OF THE INVENTION

1. Field of the Invention

This invention relates to a fluidic media introduction apparatus, and more particularly to a fluidic media introduction apparatus for closing an opening in a vessel wall.

2. Description of Related Art

Various surgical procedures utilize percutaneous entry into a blood vessel or body cavity. Examples of such procedures include different techniques to recanalize atherosclerotic blood vessels, such as balloon angioplasty or atherectomy.

These procedures generally involve the percutaneous puncture with a thin walled needle into a blood vessel. Following this, a guidewire is placed through the needle into the blood vessel and the needle is withdrawn. An intravascular sheath of variable size is then advanced over the guidewire, percutaneously, into the lumen of the blood vessel. The introducer sheath is then used as an ingress/egress means during the procedure. Following completion of the procedure, the introducer sheath may be removed, but this requires the application of prolonged manual pressure over the puncture site by a physician or other suitably trained medical personnel. The time involved here is frequently extensive since patients are often treated with a variety of anticoagulant and thrombolytic agents, particularly in the setting of a heart attach. Alternatively, the sheath may be left in the puncture site for a prolonged period of time until the patient's coagulation status has returned to normal. Depending on the size of the size of the vascular sheath, there may be an increased risk of bleeding to the patient, which may require blood transfusion. in addition, there is a significant risk for injury to the blood vessel upon removal of the sheath, particularly if the sheath has been in place for a prolonged period of time. This includes the possible development of a pseudo-aneurysm or severe hematoma. Current methods for removal of introducer sheaths are painful to the patient and requires prolonged bed rest after removal. This adds to the discomfort for the patient, as well as prolonging hospitalization, and costs.

Many of the intra-vascular procedures are performed in patients who are clinically unstable or who have the potential to become so, following completion of the procedure. Following removal of the vascular access sheath, it could be cumbersome and sometimes difficult to re-enter the blood vessel if necessary. Thus, with the current technique for removal of the sheath following the procedure, no easy, reliable method is available to allow re-access to the lumen of the blood vessel, if necessary.

It would desirable to provide a fluid delivery device which provides vascular sealing and easy re-access to the lumen of the blood vessel. It would be further desirable to provide a fluid delivery device which provides vascular sealing and includes a mixing chamber for mixing a fluidic media.

SUMMARY OF THE INVENTION

Accordingly, an object of the invention is to provide a fluid delivery device.

Another object of the invention is to provide a fluid delivery device used for vascular sealing.

A further object of the invention is to provide a fluid delivery device that delivers a fluidic media to a vascular puncture site.

Still another object of the invention is to provide a fluid delivery device with a mixing chamber and a guide wire lumen, where the fluid delivery device is used for vascular sealing.

These and other objects of the invention are achieved in a fluidic media delivery apparatus for closing an opening in a vessel wall. The apparatus includes an elongated member with a fluidic media introduction port and a guide wire lumen. The guide wire lumen extends from a proximal portion to a distal portion of the elongated member. A fluidic media mixing chamber is positioned in the elongated member and coupled to a fluidic media introduction port. A fluidic media delivery lumen is coupled to the mixing chamber. A fluidic media advancement port is positioned at the distal portion of the elongated member. An inflatable member is coupled to the distal portion of the elongated member.

DETAILED DESCRIPTION

Figure 1:
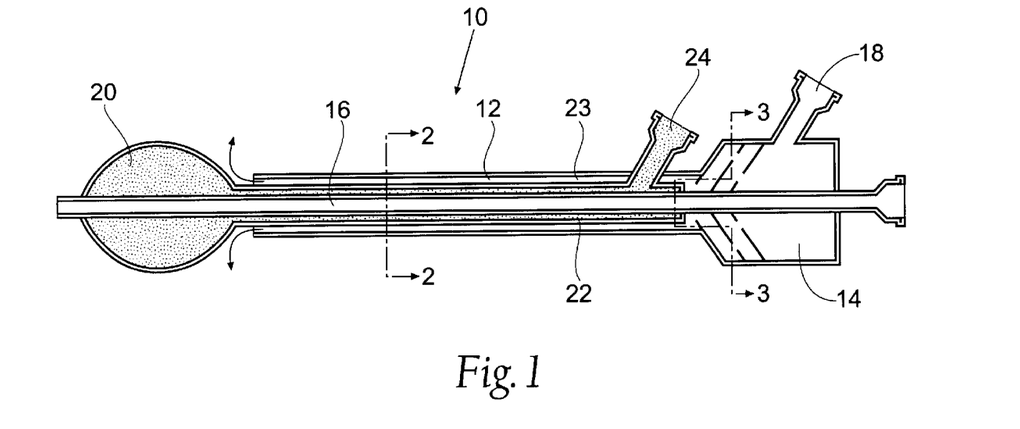
FIG. 1 is a cross-sectional view of a fluidic media delivery apparatus of the present invention with an elongated member, a guide wire lumen, a mixing chamber and a balloon coupled to a distal portion of the elongated member.
Figure 2:
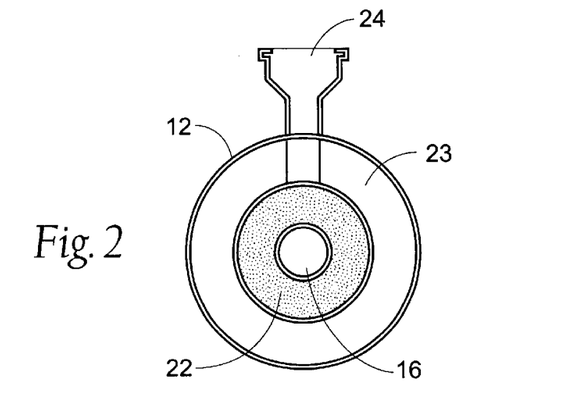
FIG. 2 is a cross-sectional view of the apparatus of FIG. 1 taken along the lines 2—2.

Referring now to FIG. 1, a fluid delivery device 10 provides for vascular sealing and includes an elongated member 12 with a mixing chamber 14, a guide wire lumen 16 and a fluidic media introduction port 18. Coupled to elongated member 12 is an expandable member 20 that is coupled to an inflation lumen 22. Inflation lumen 22 is coupled to an inflation port 24. In one embodiment, expandable member 20 is a balloon or basket that is positioned at a distal portion of elongated member 12. Balloon 20 is positioned proximal to a distal end of guide wire lumen 16. Balloon 20 can be made of a variety of materials including but not limited to PE, PET, mylon, latex and the like. Elongated member 12 can be a sheath, introducer, cannula, catheter and the like. Mixing chamber 14 may be a hub that is coupled to elongated member 12. Fluidic media introduction port 18 and inflation port 24 can have connectors including but not limited to Luer-Lock connectors. A cap can be positioned at a proximal end of elongated member 12. A guide wire port is positioned at the proximal end of elongated member 12.

Elongated member 12 is sized to be introduced over a guide wire. A distal end of elongated member 12 is positioned in a vessel through a puncture site. Proximal to balloon 20 is a fluidic media delivery port 24 coupled to a fluidic media delivery lumen 23.

Apparatus 10 is a fluid delivery device for closing a site in a vessel, including but not limited to a puncture or other opening in a blood vessel which has been entered through percutaneous techniques. Apparatus 10 can be used with a standard percutaneous vascular sheath or introducer. In a preferred embodiment, apparatus 10 is used without a sheath or introducer. In this embodiment, elongated member 12 provides substantially the same function as a sheath or introducer and also serves to deliver a suitable fluidic media to a vessel closure site.

Elongated member 12 is rigid and can have a tubular geometric configuration. A diameter of elongated member 12 is less than a diameter of an access lumen of an introducer or sheath with which it is used and a length that is preferably at least 2 cm greater than that of the introducer. Balloon 20 can be coupled to elongated member 12 by a variety of different methods well known to those skilled in the art including but not limited to heat bonding or the use of adhesives. Elongated member 12 can be made of a variety of different materials including but not limited to HDPE, polyimide, mylon, stainless steel, a shape memory alloy and combinations thereof.

Elongated member 12 is positioned through a puncture site of a vessel over a guide wire with a distal end of elongated member 12 in the vessel. An inflation media is introduced through port 24 to inflate balloon 20. Balloon 20 is then inflated when it is in an interior of the vessel. A portion of the inflated balloon 20 abuts against an interior surface of the vessel wall at the puncture site. Fluidic media is then injected through fluidic media introduction port 18. The fluidic media, which can be one or more components, is flowable and can include solid particulates. The fluidic media is advanced through mixing chamber 14 by an external pressure application force that is delivered through port 18. After the fluidic media has been mixed and advanced through mixing chamber 14, the fluidic media travels through a lumen of elongated member that is preferably in a surrounding relationship to guide wire lumen 16. The fluidic media then seals the puncture site, balloon 20 is then deflated and the distal end of elongated member 12 removed from the interior of the vessel.

If required, elongated member 12 can again be introduced into the vessel, or other body tissue or site. In this embodiment, the guide wire is received once more in guide wire lumen 16. Elongated member 12 is reintroduced through the puncture site with balloon 20 deflated.

Inflated balloon 20 blocks egress of blood immediately upon being properly positioned in the blood vessel or other tissue site at the puncture site to provide quick hemostasis. Inflated balloon 20 can also acts as an internal marker to ascertain the depth of the puncture as well as the thickness of tissues surrounding the puncture. Additionally, inflated balloon 20 serves as a backstop to precisely position the fluidic media at the puncture site and reduce the chance of fluidic media entrance into vessel or other tissue site.

Figure 3:
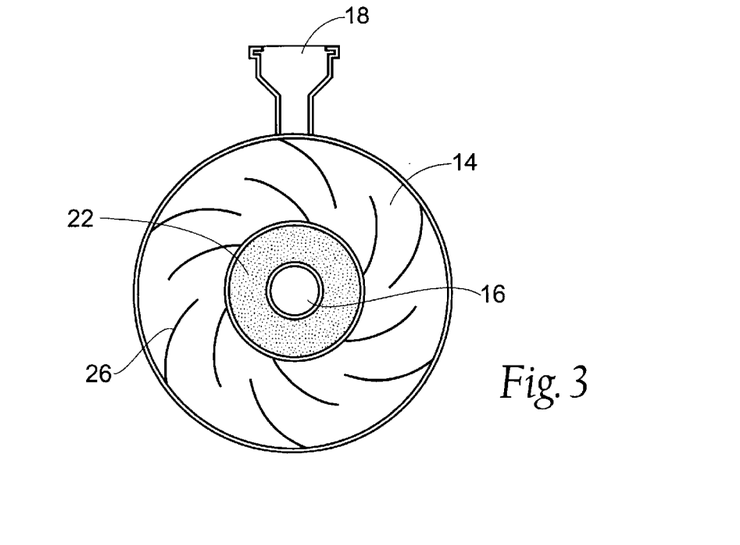
FIG. 3 is a cross-sectional view of the apparatus of FIG. 1 taken along the lines 3—3.
Figure 4:
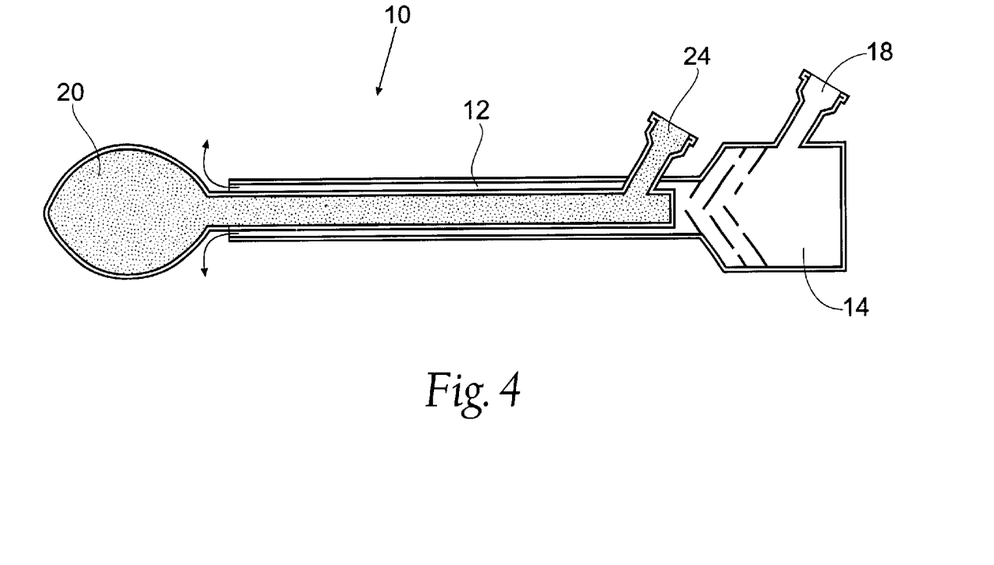
FIG. 4 is a cross-sectional view of a fluidic media delivery apparatus of the present invention similar to the apparatus of FIG. 1 but without a guide wire lumen.

FIG. 3 illustrates the cross-section of elongated member at a point that is proximal to balloon 20. In one embodiment, inflation lumen 22 is in a surrounding relationship to guide wire lumen 16. Fluidic media delivery lumen 23 is in a surrounding relationship to inflation lumen 22. FIG. 4 illustrates the cross-section of elongated member at mixing chamber 14. As shown, baffles 26 are coupled to exterior surfaces of guide wire lumen 16 and interior surfaces of mixing chamber 14. Baffles 26 are arranged in a circumferential pattern to create a circumferential and circular flow and mixing of fluidic media.

Referring now to FIG. 4, another embodiment of apparatus 10 is illustrated that does not include a guide wire lumen. In this embodiment, the distal end of elongated member 12 is introduced into the vessel without a guide wire. Balloon 20 is inflated, fluidic media introduced and mixed in mixing chamber 14 and then advanced out of port 24 to seal the puncture site.

Figure 5:
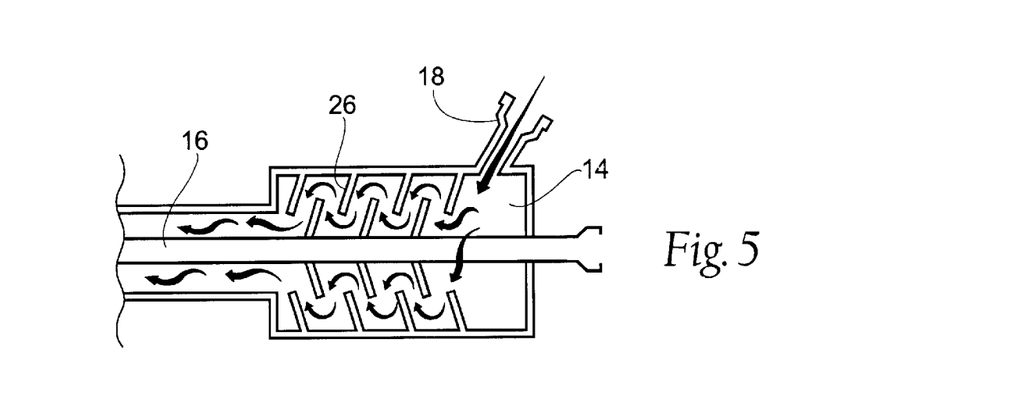
FIG. 5 is a cross-sectional view of a mixing chamber of the FIG. 1 apparatus where the mixing chamber includes baffles.
Figure 6:
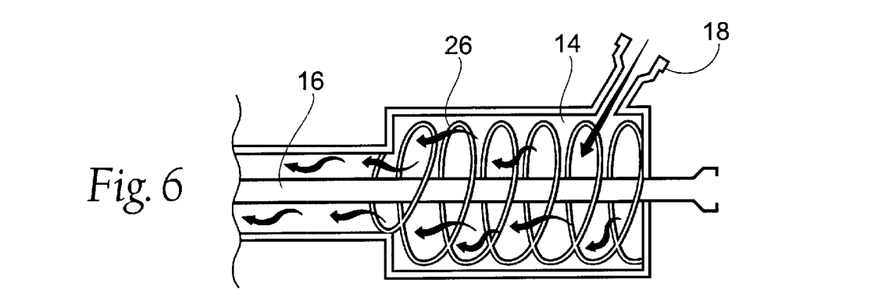
FIG. 6 is a cross-sectional view of a mixing chamber of the FIG. 1 apparatus with a spiral baffle.

As illustrated in FIGS. 5 and 6, mixing chamber 14 can include baffles that are non-spiral (FIG. 5) or in a spiral configuration (FIG. 6). Other means of mixing beyond baffles are possible. Mixing chamber 14 can be in a surrounding relationship to guide wire lumen 16 or only at one side of guide wire lumen. Additionally, mixing chamber has sufficient length to ensure the desired mixing of the fluidic media that provides the sealing of the vessel, or other tissue site.

Figure 7:
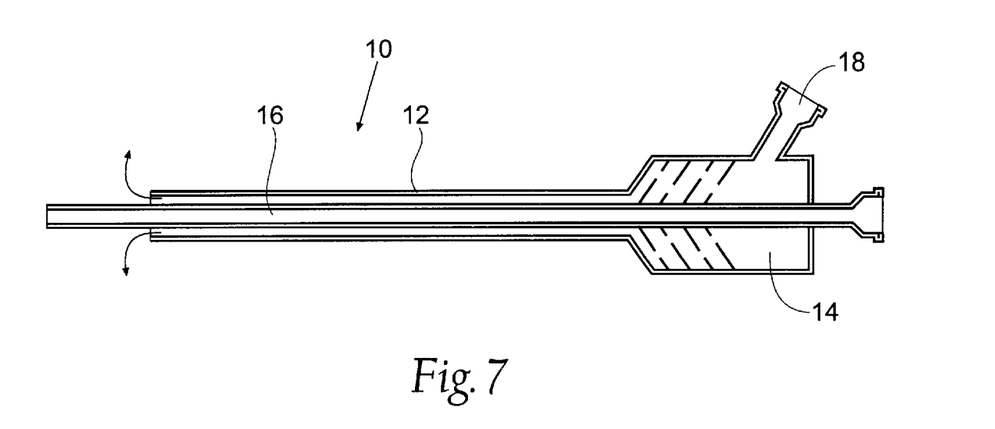
FIG. 7 is a cross-sectional view of a fluidic media delivery apparatus of the present invention similar to the apparatus of FIG. 1 but without an inflatable member at the distal portion of the elongated member.

In another embodiment, illustrated in FIG. 7, apparatus 10 does not include an expandable member 20. The distal end of guide wire lumen 16 is inserted through the puncture site. Fluidic media is mixed in mixing chamber 14 and advanced out of elongated member 12 through port 24 and seals the puncture site.

Figure 8:
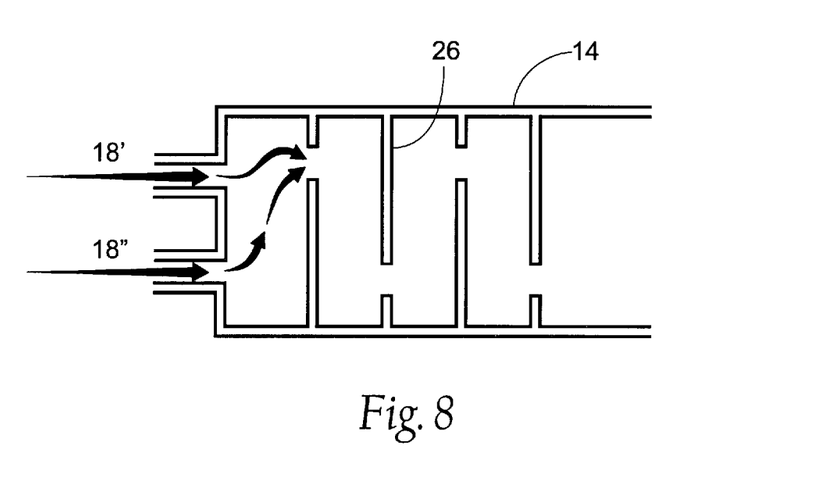
FIG. 8 is a cross-sectional view of a mixing chamber useful with the apparatus of FIG. 1, where the mixing chamber includes baffles that guide the fluidic media from one side to the other of the mixing chamber.

Another embodiment of mixing chamber 14 is illustrated in FIG. 8. In this embodiment, baffles 26 are of different sides. Baffles 26 create mixing of the fluidic media by causing fluidic media to advance and move from one side of mixing chamber to the other. In this embodiment, two ports 18' and 18" are included. The embodiment of FIG. 8 is particularly suitable for fluidic media with two separate components that are separately introduced through ports 18' and 18" respectively.

Figure 9:
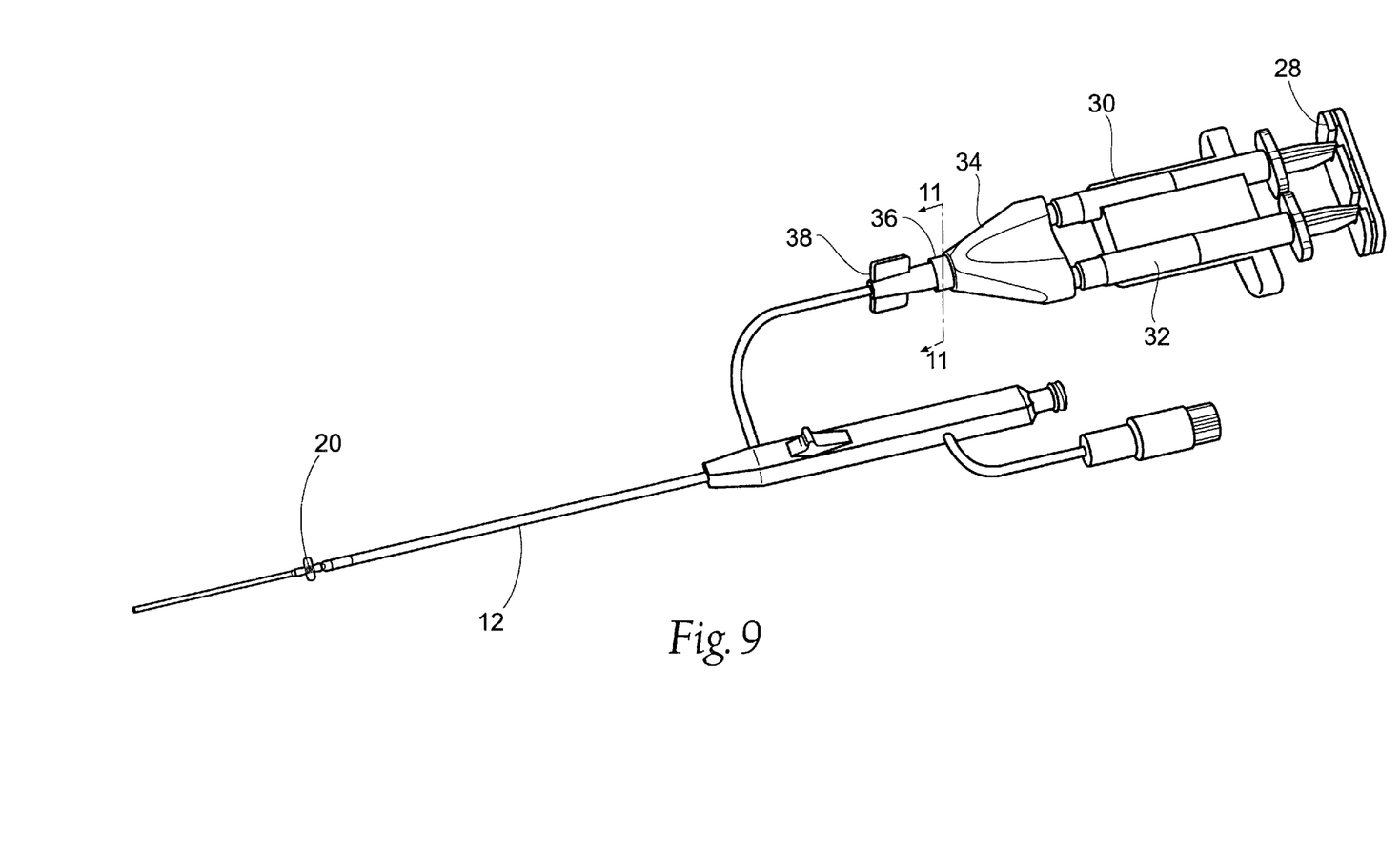
FIG. 9 is a perspective view of a fluid delivery device with a syringe clip and two syringe holders.
Figure 10:
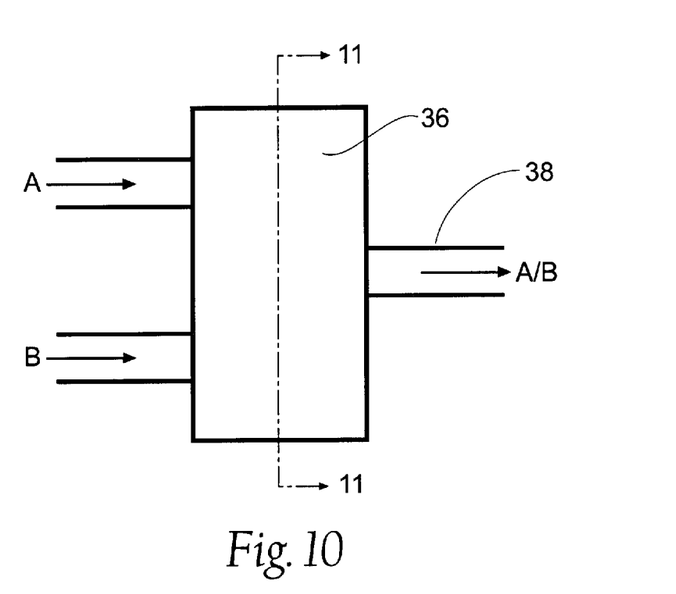
FIG. 10 is a perspective view of the mixer from the apparatus of FIG. 9.
Figure 11:
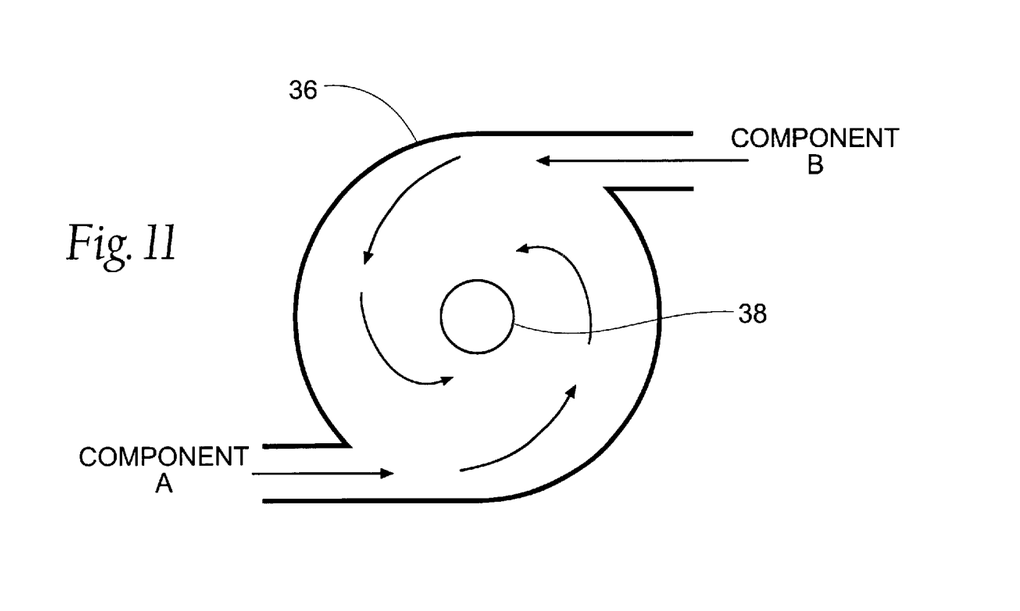
FIG. 11 is a cross-sectional view of the mixer of FIG. 10 taken along the lines 11—11.

Referring now to FIG. 9, another embodiment of apparatus 10 is illustrated. In this embodiment, a syringe clip 28 is used to introduce a two component fluidic media into lumen 23 of elongated member 12. A distal portion of syringe clip 28 is positionable in a first syringe body 30 and a second syringe body 32. First and second syringe bodies 30 and 32 are coupled to a joiner 34. Joiner 34 is coupled to a mixer 36 which in turn is connected to a nozzle 38. As illustrated in the sectional view of mixer 36 (FIG. 10), the two components that make up the fluidic media are introduced separately into mixer 36. As shown in FIG. 11, the two components travel in a swirling pattern in mixer 36 before they are ejected through nozzle 38.

Figure 12:
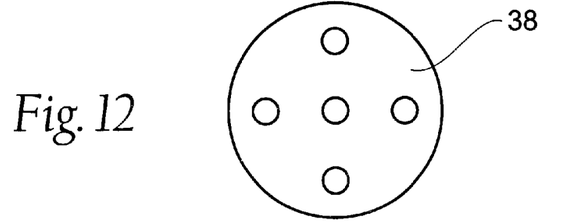
FIG. 12 is a cross-sectional view of a multiple-nozzle from the apparatus of FIG. 9.
Figure 13:
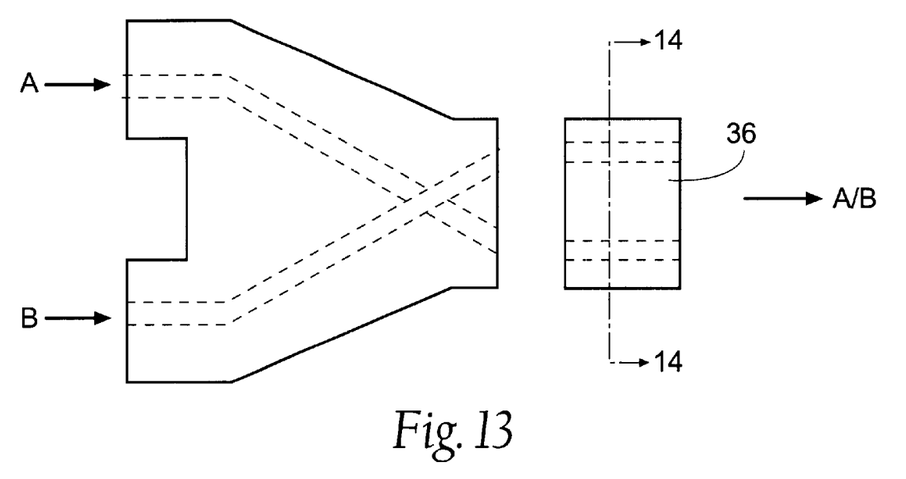
FIG. 13 is a cross-sectional view of a mixer and a joiner similar to that illustrated in FIG. 9 where the delivery ports of a two component fluidic media are separated.
Figure 14:
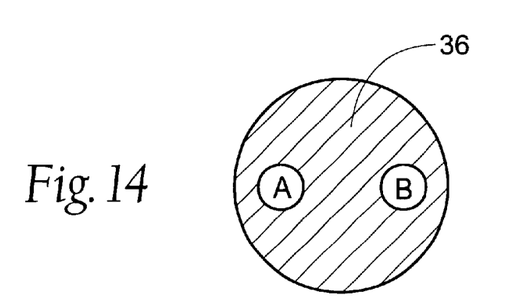
FIG. 14 is a cross-sectional view of the apparatus of FIG. 14 taken along the lines 14—14.
Figure 15:
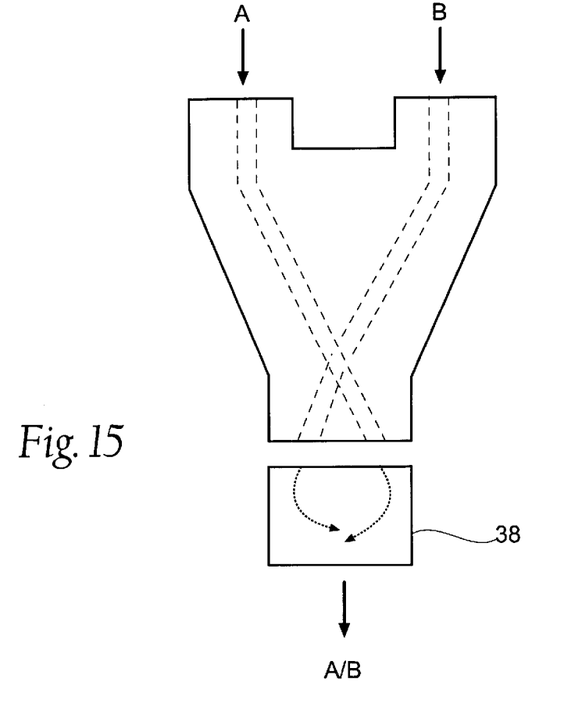
FIG. 15 is a cross-sectional view of an embodiment of the apparatus of FIG. 9 with a static mixer.

In various embodiments, nozzle 38 can have multiple spray ports (FIG. 12), and the delivery ports of mixer 36 are separated for the different components of fluidic media to be mixed (FIGS. 13 and 14). As illustrated in FIG. 15, the introduction of the two components of a dual component fluidic media are separated until they reach a deliver port and/or nozzle 38. This creates a static mixing effect at the port.

Figure 16:
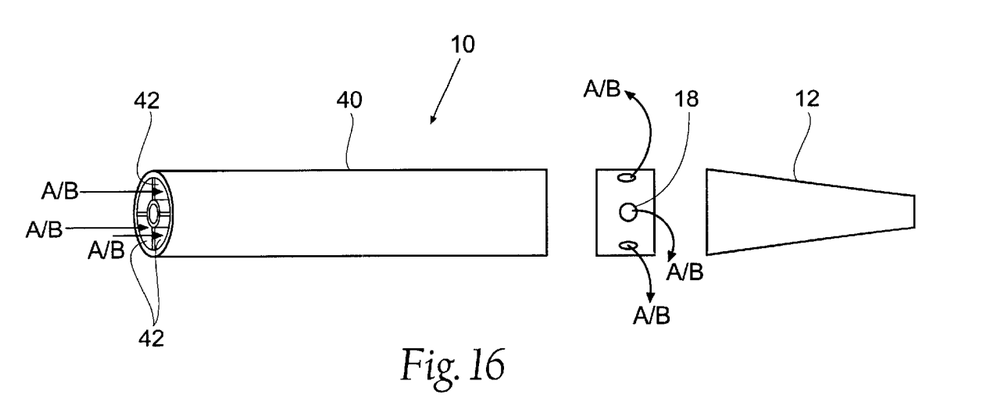
FIG. 16 illustrates a fluidic media delivery apparatus with an elongated member, delivery port and a multiple lumen fluidic media delivery coupler.
Figure 17:
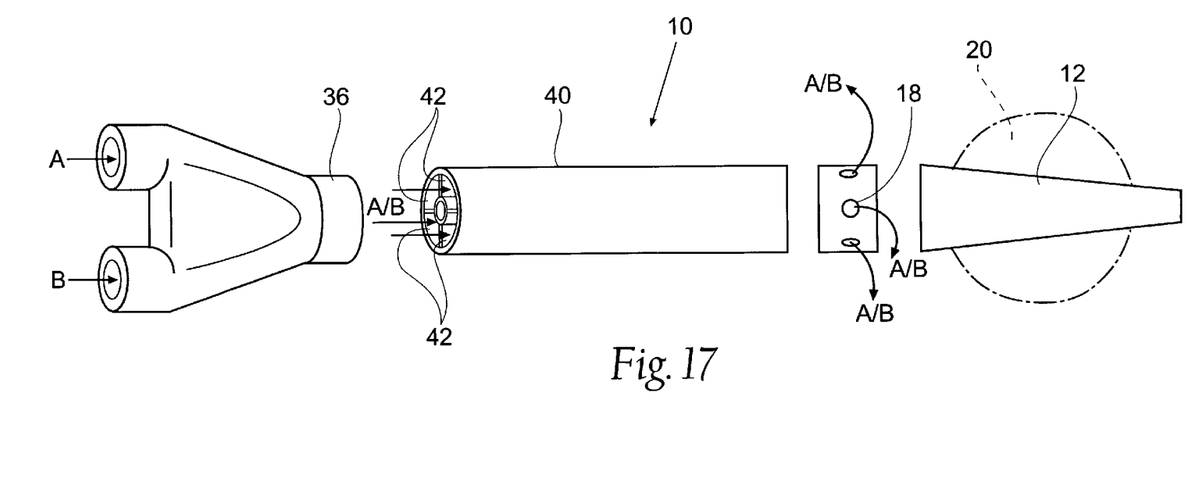
FIG. 17 illustrates a fluidic media delivery apparatus with an elongated member, delivery port and a multiple lumen fluidic media delivery coupler connected to a mixer.
Figure 18:
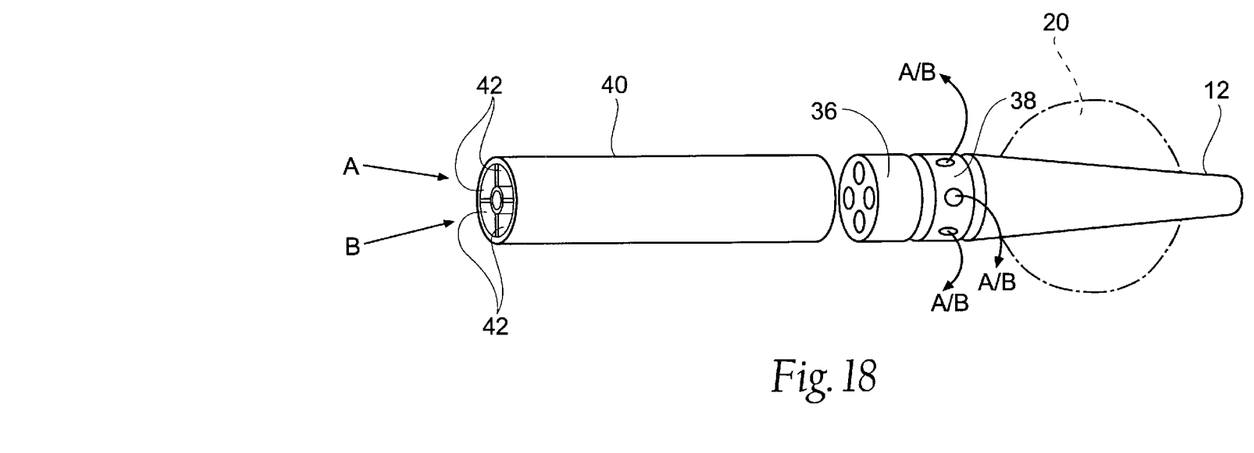
FIG. 18 illustrates a fluidic media delivery apparatus with an elongated member, delivery port and a multiple lumen fluidic media delivery coupler connected to a mixing chamber and spray nozzle.

FIGS. 16 through 18 illustrates various embodiments for mixing multiple component fluidic media that are used with apparatus 10. In FIG. 16, a multiple lumen fluidic media delivery coupler 40 includes four delivery lumens 42. Three of lumens 42 deliver the fluidic media to delivery port 18. In FIG. 17, the multiple component fluidic media is mixed in mixer 36 prior to delivery to lumens 42. In FIG. 18, multiple lumens 42 deliver the multiple component fluidic media to mixer 36, which is coupled to nozzle 38. Nozzle 38 is connected to elongated body 12.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An apparatus for introducing a closure media to seal a puncture site in a vessel comprising
   a catheter including a closure media introduction port,
   a guide wire lumen extending from a proximal portion to a distal portion of the catheter,
   a mixing chamber coupled to the closure media introduction port including a plurality of baffles positioned in an interior of the mixing chamber comprising an array of spaced apart walls,
   a closure media delivery lumen coupled to the mixing chamber, a closure media advancement port positioned at the distal portion of the catheter, and
   an inflatable member fixedly coupled to the distal portion of the catheter at a fixed distance from the closure media advancement port.

2. An apparatus for introducing a closure media to seal a puncture site in a vessel comprising
   a catheter including a closure media introduction port,
   a guide wire lumen extending from a proximal portion to a distal portion of the catheter,
   a mixing chamber coupled to the closure media introduction port including a plurality of baffles positioned in an interior of the mixing chamber, a portion of the plurality of baffles being coupled to an exterior surface of the guide wire lumen,
   a closure media delivery lumen coupled to the mixing chamber, a closure media advancement port positioned at the distal portion of the catheter, and
   an inflatable member fixedly coupled to the distal portion of the catheter at a fixed distance from the closure media advancement port.

3. The apparatus of claim 2, wherein a plurality of the baffles are coupled to an interior surface of the mixing chamber.

4. An assembly for introducing a closure material to seal a puncture site in a vessel, the closure material comprising a mixture of a first and a second fluid composition, the assembly comprising
   a catheter having a proximal end and a distal end, at least one fluid delivery port adjacent the catheter distal end to occupy a position outside the vessel adjacent the puncture site, an expandable member distal to the fluid delivery port to extend through the puncture site and occupy a position inside the vessel while the at least one fluid delivery port occupies a position adjacent the vessel puncture site outside the vessel, a fluid delivery lumen in the catheter in fluid communication with the fluid delivery port, and a guide wire lumen in the catheter sized to accommodate passage of a guide wire,
   one or more dispensers adjacent the catheter proximal end in fluid communication with the catheter lumen for dispensing the first and second fluid compositions into the catheter lumen,
   an actuator for causing the first and second fluid compositions to be dispensed from the one or more dispensers for passage through the catheter lumen, and
   a mixing chamber in a downstream flow direction from the actuator and in an upstream flow direction from the catheter lumen for mixing the first and second fluid compositions prior to passage through the catheter lumen, the mixing chamber including a plurality of baffles.

5. The assembly of claim 4
   wherein the baffles define a spiral pattern.

6. An assembly for introducing a closure material to seal a puncture site in a vessel, the closure material comprising a mixture of a first and a second fluid composition, the assembly comprising
   a catheter having a proximal end and a distal end, at least one fluid delivery port adjacent the catheter distal end to occupy a position outside the vessel adjacent the puncture site, an expandable member distal to the fluid delivery port to extend through the puncture site and occupy a position inside the vessel while the at least one fluid delivery port occupies a position adjacent the vessel puncture site outside the vessel, a fluid delivery lumen in the catheter in fluid communication with the fluid delivery port, and a guide wire lumen in the catheter sized to accommodate passage of a guide wire,
   one or more dispensers adjacent the catheter proximal end in fluid communication with the catheter lumen for dispensing the first and second fluid compositions into the catheter lumen, an actuator for causing the first and second fluid compositions to be dispensed from the one or more dispensers for passage through the catheter lumen, and a mixing chamber in a downstream flow direction from the actuator and in an upstream flow direction from the catheter lumen for mixing the first and second fluid compositions prior to passage through the catheter lumen, the guide wire lumen extending through the mixing chamber.

7. An apparatus for introducing a closure media to seal a puncture site in a vessel comprising a catheter including a closure media introduction port, a guide wire lumen extending from a proximal portion to a distal portion of the catheter, a mixing chamber coupled to the closure media introduction port, a closure media delivery lumen coupled to the mixing chamber, a closure media advancement port positioned at the distal portion of the catheter, and an inflatable member fixedly coupled to the distal portion of the catheter at a fixed distance from the closure media advancement port comprising a balloon sized to be inflatable within an interior of a blood vessel, and a plurality of baffles positioned in an interior of the mixing chamber.

8. An apparatus for introducing a closure media to seal a puncture site in a vessel comprising a catheter including a closure media introduction port, a guide wire lumen extending from a proximal portion to a distal portion of the catheter, a mixing chamber coupled to the closure media introduction port, a closure media delivery lumen coupled to the mixing chamber, a closure media advancement port positioned at the distal portion of the catheter, and an expandable member coupled to the distal portion of the catheter comprising a basket, and a plurality of baffles positioned in an interior of the mixing chamber.

9. The apparatus of claim 7 or 8, wherein the plurality of baffles are formed in a spiral pattern.

10. The apparatus of claim 7 or 8, wherein the baffles are positioned in the mixing chamber to create a swirling of the closure media in the mixing chamber.

11. An apparatus for introducing a closure media to seal a puncture site in a vessel comprising a catheter including a closure media introduction port, a guide wire lumen extending from a proximal portion to a distal portion of the catheter, a mixing chamber coupled to the closure media introduction port including a plurality of baffles positioned in an interior of the mixing chamber comprising an array of spaced apart walls, the mixing chamber being in a surrounding relationship to the guide wire lumen, a closure media delivery lumen coupled to the mixing chamber, a closure media advancement port positioned at the distal portion of the catheter, and an inflatable member coupled to the distal portion of the catheter.

12. An apparatus for introducing a closure media to seal a puncture site in a vessel comprising a catheter including a closure media introduction port, a guide wire lumen extending from a proximal portion to a distal portion of the catheter, a mixing chamber coupled to the closure media introduction port, the mixing chamber is in a surrounding relationship to the guide wire lumen, a closure media delivery lumen coupled to the mixing chamber, a closure media advancement port positioned at the distal portion of the catheter, and an inflatable member coupled to the distal portion of the catheter comprising a balloon sized to be inflatable within an interior of a blood vessel.

13. An apparatus for introducing a closure media to seal a puncture site in a vessel comprising a catheter including a closure media introduction port, a guide wire lumen extending from a proximal portion to a distal portion of the catheter, a mixing chamber coupled to the closure media introduction port, the mixing chamber being in a surrounding relationship to the guide wire lumen, a closure media delivery lumen coupled to the mixing chamber, a closure media advancement port positioned at the distal portion of the catheter, and an expandable member coupled to the distal portion of the catheter comprising a basket.

14. An apparatus for introducing a closure media to seal a puncture site in a vessel comprising a catheter including a closure media introduction port, a guide wire lumen extending from a proximal portion to a distal portion of the catheter, a mixing chamber coupled to the closure media introduction port including a plurality of baffles positioned in an interior of the mixing chamber comprising an array of spaced apart walls, the mixing chamber being in a surrounding relationship to the guide wire lumen, a closure media delivery lumen coupled to the mixing chamber, a closure media advancement port positioned at the distal portion of the catheter, and an expandable member coupled to the distal portion of the catheter.

* * * * *

UNITED STATES PATENT AND TRADEMARK OFFICE
CERTIFICATE OF CORRECTION

PATENT NO. : 6,475,182 B1
DATED : November 5, 2002
INVENTOR(S) : Olexander Hnojewyj et al.

It is certified that error appears in the above-identified patent and that said Letters Patent is hereby corrected as shown below:

Title page,
Item [54], Title, delete " FLUIDIC MEDIA INTRODUCTION APPARATUS" and substitute -- ASSEMBLIES FOR INTRODUCING CLOSURE MATERIAL TO SEAL A VESSEL PUNCTURE SITE --.
Item [56], References Cited, insert the following:

U.S. PATENT DOCUMENTS

| | | | | | |
|---|---|---|---|---|---|
| 4,424,833 | 1/1984 | Spector et al. | 5,053,046 | 10/1991 | Janese |
| 4,555,242 | 11/1985 | Saudager | 5,061,274 | 10/1991 | Kensey |
| 4,738,658 | 4/1988 | Magro et al. | 5,108,421 | 4/1992 | Fowler |
| 4,744,364 | 5/1988 | Kensey | 5,129,882 | 7/1992 | Weldon et al. |
| 4,838,280 | 6/1989 | Haaga | 5,156,613 | 10/1992 | Sawyer |
| 4,852,568 | 8/1989 | Kensey | 5,159,937 | 11/1992 | Tremulis |
| 4,874,368 | 10/1989 | Miller et al. | 5,163,906 | 11/1992 | Ahmadi |
| 4,890,612 | 1/1990 | Kensey | 5,171,222 | 12/1992 | Euteneuer et al. |
| 4,891,359 | 1/1990 | Saferstein eta l. | 5,192,300 | 3/1993 | Fowler |
| 5,002,051 | 3/1991 | Dew et al. | 5,197,971 | 3/1993 | Bonutti |
| 5,021,059 | 6/1991 | Kensey et al. | 5,221,259 | 6/1993 | Weldon et al. |
| 5,041,129 | 8/1991 | Hayhurst et al. | 5,222,974 | 6/1993 | Kensey et al. |
| 5,042,985 | 8/1991 | Elliott et al. | 5,250,025 | 10/1993 | Sosnowski et al |

| | | |
|---|---|---|
| 5,275,616 | 1/1994 | Fowler |
| 5,281,197 | 1/1994 | Arias et al. |
| 5,282,827 | 2/1994 | Kensey et al. |
| 5,290,310 | 3/1994 | Makower et al |
| 5,292,309 | 3/1994 | Van Tassel et al |
| 5,292,332 | 3/1994 | Lee |
| 5,306,254 | 4/1994 | Nash et al. |
| 5,324,306 | 6//1994 | Makower et al |
| 5,383,896 | 1/1995 | Gershony et al |
| 5,411,520 | 5/1995 | Nash et al. |
| 5,413,571 | 5/1995 | Katsaros et al. |
| 5,415,657 | 5/1995 | Taymor-Luria |
| 5,419,765 | 5/1995 | Weldon et al. |
| 5,437,292 | 8/1995 | Kipshidze et al |
| 5,441,517 | 8/1995 | Kensey et al. |
| 5,447,502 | 9/1995 | Haga |
| 5,486,195 | 1/1996 | Myers et al. |
| 5,496,332 | 3/1996 | Sierra et al. |
| 5,575,815 | 11/1996 | Slepian et al. |
| 5,591,204 | 1/1997 | Janzen et al. |
| 5,591,205 | 1/1997 | Fowler |
| 5,601,602 | 2/1997 | Fowler et al. |
| 5,612,050 | 3/1997 | Rowe et al. |
| 5,626,601 | 5/1997 | Gershony et al |
| 5,630,833 | 5/1997 | Katsaros et al. |
| 5,649,959 | 7/1997 | Hannam et al. |
| 5,653,730 | 8/1997 | Hammerslag |
| 5,665,106 | 9/1997 | Hammerslag |
| 5,665,107 | 9/1997 | Hammerslag |
| 5,669,934 | 9/1997 | Sawyer |

OTHER DOCUMENTS

Abergelm R.P. et al., "Skin Closure by Nd:YAG Laser Welding" American Academy of Dermatology. 1986 14 (5):810-14

Anand, R.K. et.al.; "Laser Balloon Angioplasty: Effect of Constant Temperature Versus Constant Power on Tissue Weld Strength", Lasers in Surgery and Medicine, 1988 8(1):40-44

Chuck, R.S. et al., "Dye-Enhanced Laser Tissue Welding", Lasers in Surgery and Medicine. 1989 9(5):471-477

Fujitani, R.M. et al., "Biophysical Mechanisms of Argon Laser-Assisted Vascular Anastomosis", Current Surgery, March-April 1988. P119-123

Goldstein, J.D. et al., "Development of a Reconstituted Collagen Tendon Prosthesis", The Journal of Bone and Joint Surgery. 1989 71-A(8):1183-91

UNITED STATES PATENT AND TRADEMARK OFFICE
CERTIFICATE OF CORRECTION

PATENT NO.   : 6,475,182 B1
DATED        : November 5, 2002
INVENTOR(S)  : Olexander Hnojewyj et al.

It is certified that error appears in the above-identified patent and that said Letters Patent is hereby corrected as shown below:

Title page (cont'd),

| | | |
|---|---|---|
| 5,676,689 | 10/1997 | Kensey et al. |
| 5,700,273 | 12/1997 | Buelna et al. |
| 5,725,498 | 3/1998 | Janzen et al. |
| 5,725,551 | 3/1998 | Myers et al. |
| 5,728,132 | 3/1998 | VanTassel et al |

FOREIGN PATENT DOCUMENTS

| | | |
|---|---|---|
| 91/09641 | 7/1991 | PCT |
| 92/22252 | 12/1992 | PCT |
| 0482350A2 | 4/1992 | Europe |
| 0482350B1 | 12/1996 | Europe |
| 0476178A1 | 3/1992 | Europe |
| 0330344 | 2/1988 | Europe |
| 1569660 | 7/1977 | Great Britain |

Kopchok, G. et al., "Argon Laser Vascular Welding: The Thermal Component" SPIE. 1985. 712:260-3

Kopchok, G. et al., "Thermal Studies of In-Vivo Vascular Tissue Fusion by Argon Laser", Journal of Investigative Surgery, 1988. 1:5-12.

Kopchok, G. et al., "CO2 and Argon Laser Vascular Welding: Acute Histologic and Thermodynamic Comparison". Lasers in Surgery and Medicine. 1988. 8:584-8

Lemole, G.M. et al., "Preliminary Evaluation of Collagen as a Component in the Thermally Induced 'Weld'", SPIE. 1991 1422:116-22

Mininberg, D.T. et al., "Laser Welding of Perdicled Flap Skin Tubes", The Journal of Urology, 1989. 142(2):623-5

Murray, L.W. et al., "Crosslinking of Extracellular Matrix Proteins", Lasers in Surgery and Medicine. 1989. 9:490-6

Grubbs, P.E. et al., "Determinants of Weld Strength in Laser-Assisted Microvascular Anastomosis", Current Surgery, Jan-Feb 1989 p. 3-5

Grubbs, P.E. et al., "Enhancement of CO2 Laser Microvascular Anastomosis by Fibrin Glue", Journal of Surgical Research 1988. 45:112-119

Jain, K.K. et al., "Repair of Small Blood Vessels With the Neodymium-YAG Laser: A Preliminary Report", Surgery 85(6):684-8

Oz, M.C. et al., "In Vitro Comparison of Thulium-Holmium-Chromium-YAG and Argon Ion Lasers for Welding of Billiary Tissue", Lasers in Surgery and Medicine. 1989. 9:248-53

Gilbert, P.T. et al., "Laser-Assisted Vasovasostomy", 1989. 9:42-44

Poppas. D.P. et al., "Laser Welding in Urethral Surgery: Improved Results with a Protein Solder", The Journal of Urology 1988 139:415-17.

Schober, R. et al., "Laser-Induced Alteration of Collagen Substructure Allows Microsurgical Tissue Welding", Science, June 1986. 232:1421-2

Tanzer, M.L. et al., "Cross-Linking of Collagen", Science. 180:561-6

Vale, B.H. et al., "Microsurgical Anastomosis of Rat Carotid Arteries With the CO2 Laser", Plastic and Re-constructive Surgery. 77(5):759-66

White, R.A. et al., "Argon Laser-Welded Arteriovenous

UNITED STATES PATENT AND TRADEMARK OFFICE
CERTIFICATE OF CORRECTION

PATENT NO. : 6,475,182 B1
DATED : November 5, 2002
INVENTOR(S) : Olexander Hnojewyj et al.

It is certified that error appears in the above-identified patent and that said Letters Patent is hereby corrected as shown below:

Title page (cont'd),

Nimni, M.E., "Third International Congress of Biorhology Symposium of the Soft Tissues Around a Diarthrodial Joint", Biorheology. 1980. 17:51-82

Oz, M.C. et al., "Tissue Soldering by Use of Indocyanine Green Dye -Enhanced Fibrinogen with the Near Infrared Diode Laser", Journal of Vascular Surgery. 1990. 11(5):718-25

Anastomosis", Journal of Vascular Surgery, 187.6(5):447-53

White, R.A. et al., "Comparison of Laser-Welded and Sutured Arteriotomies", Arch Surg. 1986. 121:-1133-5

DeCosste, S.D. et. Al., "Dye-Enhanced Laser Wedling for Skin Closure", Lasers in Surgery and Medicine, 1992. 12:35-32

White, R.A.. Et. Al., "Mechanism of Tissue Fusion in Argon Laser-Welded Vein-Artery Anastomosis", Lasers in Surgery and Medicine, 1988. 8:83-9.

Signed and Sealed this

Nineteenth Day of April, 2005

JON W. DUDAS
*Director of the United States Patent and Trademark Office*